BLUEGRASS PLANT

Filed Nov. 5, 1973

United States Patent Office

Plant Pat. 3,643
Patented Oct. 15, 1974

3,643
BLUEGRASS PLANT

Kevin Joseph McVeigh, Box 1741, State Highway 27, Somerset, N.J. 08873, and Cyril Reed Funk, Jr., 4 Delaware Drive, East Brunswick, N.J. 08816

Filed Nov. 5, 1973, Ser. No. 413,027
Int. Cl. A01h 5/12
U.S. Cl. Plt.—88 1 Claim

ABSTRACT OF THE DISCLOSURE

A Kentucky bluegrass plant which exhibits good to excellent resistance to powdery mildew, leaf rust, stripe smut and the Helminthosporium leaf spot and crown rot disease. The plant has an attractive, moderately dark green color, rather wide leaves and produces an exceptionlly vigorous, aggressive, dense turf.

Figure 1:
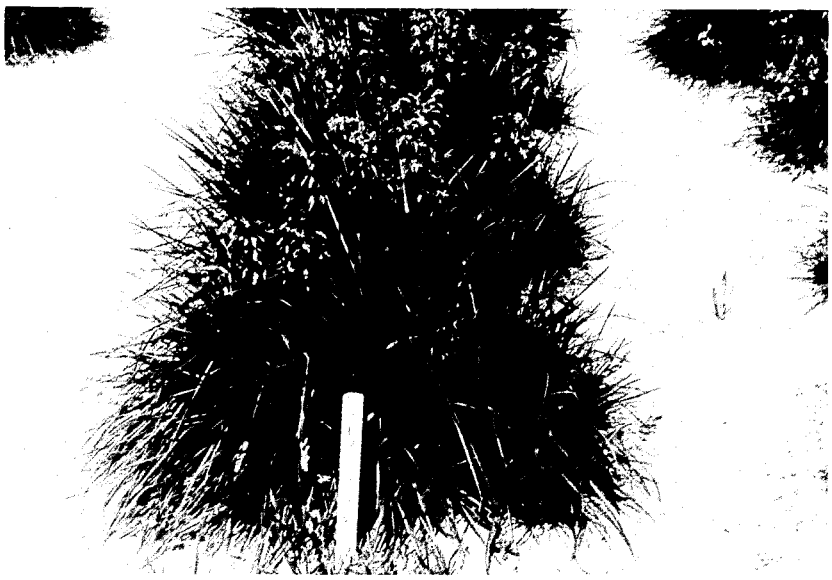

This invention relates to a new and distinct variety of Kentucky bluegrass plant, and more particularly to a bluegrass plant which produces a very dense, exceptionally aggressive turf with stiff, wide leaves and excellent resistance to stripe smut and the Helminthosporium leaf spot and crown rot disease.

The new variety was originated by us by crossing an unpatented selection identified in our breeding records as "A–25" with "Anheuser Dwarf" (U.S. Plant Pat. 3,135), "A–25" being the seed parent and "Anheuser Dwarf" being the pollen parent. As a result of this breeding, we have produced and asexually propagated by rhizomes, tillers and disseminules a new and improved variety which is distinct from each of its parents, as well as all other varieties of which we are aware. The plants of the new variety were labelled "NJE P–104" Kentucky bluegrass.

NJE P–104 has exhibited at least the following distinguishing characteristics:

1. Excellent rhizome and tiller development under turf maintenance, producing a very dense, aggressively spreading turf;
2. A moderately dark green color;
3. Broad, stiff leaves;
4. A leafy turf-type growth habit tolerant of moderately close mowing;
5. Excellent resistance to the leaf spot and crown rot disease caused by the fungus, *Helminthosporium vagans;*
6. Excellent resistance to the stripe smut disease incited by the fungus, *Ustilago striiformis;*
7. Good resistance to the powdery mildew disease caused by the fungus, *Erysiphe graminis;*
8. Very good resistance to the leaf rust disease caused by the fungus, *Puccinia poae-nemoralis;*
9. An erect panicle; and
10. Very good performance in turfgrass evaluation trials at New Brunswick, New Jersey.

In comparison with its seed parent, A–25, the new variety has wider leaves, better resistance to powdery mildew and a much higher degree of apomictic reproduction.

In comparison with its pollen parent, Anheuser Dwarf, the new variety has better seedling vigor and produces a denser turf of greater aggressiveness.

A primary object of this invention is to provide a new and distinct bluegrass plant having the desirable characteristics refered to above and to be described in detail below. Other objects and advantages of this invention will become more fully apparent from the following detailed description when taken in conjunction with the accompanying illustration, in which figure 1 shows a plant of the new variety after the completion of anthesis.

PLANT DESCRIPTION

P–104 Kentucky bluegrass (*Poa pratensis* L.) is perennial with creeping rhizomes forming a very dense, aggressive turf. Culms are moderately bent at lower nodes subsequently becoming erect, tufted and average 63 cm. in height when undisturbed by mowing, fairly stout, cylindrical, generally having 4 to 5 nodes, smooth. Leaves are moderaeely dark green; sheaths smooth with those on the vegetative shoots compressed and keeled, hairless; ligules membraneous and very short on vegetative tillers but about 1.0 to 1.5 mm. long on reproductive tillers; edge of collar lightly fringed with fine hairs; blades 4 to 6 mm. wide initially folded but subsequently opening out with a boat-shaped tip. Panicles pyramidal, open, with main axis erect averaging 112 mm. long; lower branches mostly in clusters of 4 or 5 (averaging 4.7)—spikelets ovate, compressed, 4.6 to 5.6 mm. long (average 5.0 mm.) and 1.6 to 2.5 mm. wide (average 2.1 mm.), 3 to 6-flowered, breaking up at maturity beneath each lemna. Glumes persistent, slightly pointed, unequal with rough keels; lower glume 2.9 to 3.2 mm. long (average 3.0 mm.), upper glume 2.5 to 3.0 mm. long (average 2.6 mm.), both glumes with 3 nerves. Lemmas overlapping at first, later with incurved margins, slightly pointed in sideview, 2.6 to 3.1 mm. long (average 2.9 mm.), keeled with short hairs on the keel up to about the middle and long crinkled hairs at the base, distinctly 5-nerved Paleas 2.1 to 2.8 mm. long (average 2.5 mm.). Grain 1.4 to 1.9 mm. long (average 1.6 mm.) enclosed by the hardened lemma and palea.

Since environmental factors influence morphological characteristics to some degree these characters may vary slightly under different conditions. The morphological characteristics of NJE P–104 and other bluegrasses measured during 1970 at Adelphia, N.J., are shown in Table 1.

TURF CHARACTERISTICS

The new variety has exhibited consistently high turf performance ratings. The turf is attractive, aggressive and dense.

Overall turf performance ratings for NJE P–104 and other bluegrasses for the years through 1970 at New Brunswick, N.J., are presented in Table 2.

The new variety has demonstrated consistently high turf performance ratings. Of particular significance is its high density and excellent aggressiveness, as shown in tables 3 and 4.

DISEASE RESISTANCE

A comparison of NJE P–104 and other bluegrasses for resistance to leaf spot and crown rot caused by the fungus *Helminthosporium vagans,* stripe smut caused by the fungus *Ustilago striiformis,* powdery mildew caused by the fungus *Erysiphe graminis* and leaf rust caused by the fungus *Puccinia poae-nemoralis* is presented in the following tables:

TABLE 1. MORPHOLOGICAL COMPARISON OF NJE P-57 AND OTHER BLUEGRASS VARIETIES AT ADELPHIA, N.J.

| Variety | Plant height, cm. | Plant diameter, cm. | Leaf blade width, mm. | Flag leaf length, mm. | Number of panicles per plant | Panicle color [1] | Panicle erect or nodding [2] | Number of branches at lowest panicle node | Panicle length, mm. |
|---|---|---|---|---|---|---|---|---|---|
| NJE P-104 | 63 | 34 | 5.2 | 76 | 61 | 1.5 | 1.5 | 4.7 | 112 |
| Delta | 73 | 17 | 2.6 | 67 | 196 | 2.0 | 1.0 | 4.8 | 100 |
| Geary | 80 | 24 | 2.9 | 80 | 177 | 3.0 | 3.0 | 4.0 | 134 |
| Newport | 79 | 30 | 4.8 | 77 | 246 | 2.5 | 2.0 | 4.3 | 105 |
| Palouse | 79 | 24 | 3.0 | 93 | 151 | 3.0 | 3.5 | 4.4 | 92 |
| Anheuser Dwarf (Pat. 3,135) | 67 | 30 | 5.1 | 51 | 109 | 3.0 | 2.5 | 3.4 | 96 |
| Eelturf | 70 | 35 | 3.0 | 58 | 201 | 2.0 | 2.0 | 4.0 | 104 |
| Fylking (Pat. 2,887) | 60 | 34 | 4.0 | 68 | 164 | 3.5 | 5.0 | 4.9 | 118 |
| Merion | 70 | 24 | 4.3 | 69 | 280 | 2.0 | 1.5 | 3.5 | 102 |
| Pennstar | 59 | 34 | 3.7 | 66 | 132 | 3.5 | 4.0 | 4.5 | 106 |

[1] Scale: 0=green; 5=purple.
[2] Scale: 1=erect; 5=nodding.

TABLE 2. TURF PERFORMANCE OF NJE P-104 AND OTHER BLUEGRASS VARIETIES

| Variety | Turf Performance Score (9=best) | | | | |
|---|---|---|---|---|---|
| | 1967 | 1968 | 1969 | 1970 | Ave. |
| NJE P-104 | 8.2 | 8.5 | 8.4 | 8.4 | 8.4a [1] |
| Fylking | 6.8 | 8.0 | 7.4 | 7.0 | 7.3b |
| Pennstar | 6.7 | 8.0 | 7.4 | 7.0 | 7.3b |
| Anheuser Dwarf | 6.8 | 7.0 | 7.2 | 7.5 | 7.1b |
| Merion | 6.6 | 7.1 | 4.9 | 3.1 | 5.4c |
| Park | 4.8 | 4.6 | 3.0 | 3.6 | 4.0d |
| Kenblue | 3.8 | 4.2 | 2.6 | 2.6 | 3.3d |

[1] Values followed by the same letter do not differ significantly at the five percent probability level.

Table 3. Density ratings of NJE P-104 and other bluegrasses under turf maintenance at New Brunswick, N.J.

| Variety | Density Rating 9=most dense |
|---|---|
| NJE P-104 | 8.6a [1] |
| Merion | 7.0b |
| Anheuser Dwarf | 6.5b |
| Kenblue | 4.3c |

[1] See footnote to Table 2.

Table 4. Aggressiveness of various bluegrass varieties as measured by their ability to spread under conditions of close mowing and competition from other bluegrasses

| Variety | Amount of incroachment into adjacent bluegrass varieties, "inches" |
|---|---|
| NJE P-104 | +22.0a [1] |
| Glade (Plant Pat. 3,151) | +10.5b |
| Fylking | +3.0c |
| Anheuser Dwarf | +3.0c |
| Merion | −2.0cd |
| Kenblue | −4.0d |
| Park | −4.0d |

[1] See footnote to Table 2.

Table 5. Relative comparison of leaf spot and crown rot disease level of NJE P-104 and other bluegrasses at New Brunswick, N.J.

| Variety | Percent leaf spot damage |
|---|---|
| NJE P-104 | 5a [1] |
| Anheuser Dwarf | 5a |
| Fylking | 11ab |
| Merion | 21bc |
| Park | 88d |
| Kenblue | 92d |

[1] See footnote to Table 2.

TABLE 6. RELATIVE COMPARISON OF STRIPE SMUT DISEASE INCIDENCE OF NJE P-104 AND OTHER BLUEGRASSES IN NEW JERSEY

| Variety | Stripe smut infected tillers per square foot | |
|---|---|---|
| | May 1969 | May 1970 |
| NJE P-104 | 0a [1] | 0a |
| Anheuser Dwarf | 1a | 1a |
| Fylking | 3a | 2a |
| Windsor (Plant Pat. 2,364) | 110b | 160b |
| Merion | 230c | 580c |

[1] See footnote to Table 2.

Table 7. Relative comparison of powdery mildew disease level of NJE P-104 and other bluegrasses in New Jersey

| Variety | Reaction to mildew [1] |
|---|---|
| Anheuser Dwarf | 0.0a [2] |
| NJE P-104 | 1.2b |
| A-25 | 7.8c |
| Merion | 8.1c |

[1] Scale: 0=no mildew; 9=most disease.
[2] See footnote to Table 2.

Table 8. Relative comparison of leaf rust disease level of NJE P-104 and other bluegrasses in New Jersey during 1970

| Variety | Rust disease rating [1] |
|---|---|
| NJE P-104 | 0.5a [2] |
| Anheuser Dwarf | 0.6a |
| Fylking | 1.5b |
| Warren's A-25 | 2.0b |
| Newport | 3.5c |
| Merion | 3.5c |
| Vantage | 7.5d |

[1] Scale: 0=no rust; 9=most disease.
[2] See footnote to Table 2.

The tests summarized in the foregoing tables show that NJE P-104 has excellent resistance to leaf spot, excellent resistance to stripe smut, good resistance to powdery mildew and very good resistance to leaf rust.

REPRODUCTION AND PROPAGATION

Asexual reproduction of NJE P-104 by propagules (tillers and rhizomes) and by disseminules (modified caryopses produced by agamospermy) has consistently produced progeny plants indistinguishable from the mother plant.

What is claimed is:

1. A new and distinct selection of Kentucky bluegrass plant, substantially as herein shown and described, characterized by very good performance as a turfgrass, an aggressively spreading dense turf and good to excellent resistance to important diseases.

No references cited.